United States Patent [19]
Altendorf et al.

[11] Patent Number: 5,726,751
[45] Date of Patent: Mar. 10, 1998

[54] SILICON MICROCHANNEL OPTICAL FLOW CYTOMETER

[75] Inventors: Eric H. Altendorf; Paul Yager, both of Seattle, Wash.

[73] Assignee: University of Washington, Seattle, Wash.

[21] Appl. No.: 534,515

[22] Filed: Sep. 27, 1995

[51] Int. Cl.$^6$ ..................................... G01N 1/10
[52] U.S. Cl. ............... 356/246; 356/440; 422/82.05; 422/82.09
[58] Field of Search .................. 356/244, 246, 356/335–343, 440; 422/82.05, 82.09, 68.1

[56] References Cited

U.S. PATENT DOCUMENTS

| | | | |
|---|---|---|---|
| 4,245,907 | 1/1981 | Rosen | 356/246 |
| 4,823,168 | 4/1989 | Kamahori et al. | 356/246 |
| 4,867,946 | 9/1989 | Gross et al. | 422/68 |
| 4,908,112 | 3/1990 | Pace | 204/299 |
| 4,983,038 | 1/1991 | Ohki et al. | 356/246 |
| 5,587,128 | 12/1996 | Wilding et al. | 422/50 |
| 5,593,838 | 1/1997 | Zanzucchi et al. | 435/6 |
| 5,599,503 | 2/1997 | Manz et al. | 422/82.05 |

OTHER PUBLICATIONS

Kikuchi, Y. et al. (1992), *"Optically Accessible Microchannels Formed in a Single–Crystal Silicon Substrate for Studies of Blood Rheology,"* Microvascular Res. 44:226–240.

Shapiro, H.M. et al., "Flow Cytometers Using Optical Waveguides in Place of Lenses for Specimen Illumination and Light Collection," Cytometry (1986) 7:221–223.

Miyake, R. et al., "A Development of Micro Sheath Flow Chamber," in *Proceedings of the IEEE Micro Electro Mechanical Systems Workshop*, pp. 265–270, Nara, Japan (Jan. 1991).

Verpoorte, E. et al., "A silicon flow cell for optical detection in miniaturized total chemical analysis systems," Sensors and Actuators B (1992) 6:66–70.

Kikuchi, Y. et al., "Optically accessible microchannels formed in single–crystal silicon substrates for studies of blood rheology," Microvasc. Res. (1992) 44:226–240.

Sobek, D. et al., "A Microfabricated Flow Chamber for Optical Measurements in Fluids," in *Proceedings of the IEEE Micro Electro Mechanical Systems Workshop*, Ft. Lauderdale, FL pp. 219–224 (Feb. 1993).

Wilding, P. et al., "Manipulation and Flow of Biological Fluids in Straight Channels Micromachined in Silicon," Clin. Chem. (1994) 40/1:43–47.

Sobek, D. et al., "Microfabricated Fused Silica Flow Chambers for Flow Cytometry,"Solid–State Sensors and Actuators Workshop, Hilton Head, SC, (Jun. 1994).

*Primary Examiner*—Hoa Q. Pham
*Attorney, Agent, or Firm*—Greenlee, Winner & Sullivan, P.C.

[57] ABSTRACT

The present invention provides a flow cytometer made of two components: a flow cytometer optical head and a disposable flow module. The flow module utilizes a V-groove flow channel micromachined in a silicon wafer. The optical head comprises a laser to provide an illuminating beam and small and large angle photodetectors. Anisotropically etched facets of the V-groove reflect the illuminating beam. Small angle scattered light is also reflected by the V-groove wall and is collected by the small angle photodetector. Large angle scattered light and fluorescent light can exit the channel without reflection and are collected by the large angle photodetector. In addition, fluorescent light can be back-reflected by the V-groove, which enhances the collection efficiency.

62 Claims, 6 Drawing Sheets

SILICON MICROCHANNEL OPTICAL FLOW CYTOMETER

This invention was made with Government support under contract DAMD17-94-J-440 awarded by the U.S. Army. The Government has certain right in the invention.

FIELD OF THE INVENTION

This invention relates to optical flow cytometry using a silicon microfabricated flow channel.

BACKGROUND OF THE INVENTION

Flow cytometry is a sensitive and versatile probe of the optical characteristics of microscopic biological particles, with widespread applications including hematology, immunology, genetics, food science, pharmacology, microbiology, parasitology and oncology. Optical flow cytometers use light scattering and fluorescence to determine physical and chemical properties of the particles. For measurement, particles are arranged in single file, typically by hydrodynamic focussing within a sheath fluid, and interrogated by a light beam propagating orthogonal to the flow axis. Scattered light is measured in a near forward direction by a photodetector. In addition, a second photodetector is often positioned at 90° to the forward scattering direction to collect large angle scattering and fluorescence.

Existing commercial cytometers are large and complicated instruments requiring skilled operators. To increase the accessibility of flow cytometry, microfabricated flow cells and compact cytometers are desired. In a microfabricated flow channel, a challenge is to get illuminating light into the channel and to get both forward scattered and 90° scattered light out of the channel. A few microfabricated flow cytometer flow channels have been reported. Miyake et al. [Proceedings of the IEEE Micro Electro Mechanical Systems Workshop, pp. 265–270, Nara, Japan, January 1991] describe a micromachined sheath flow channel made of five stacked plates. Three metal plates are used to create a flow having a sample core within a sheath, and glass plates on the top and bottom of the stack provide optical access to the flow channel for illumination through the top and forward scattered light collection through the bottom. Ninety degree scattering cannot be collected. Sobek et al. [Proceedings of the IEEE Micro Electro Mechanical Systems Workshop, pp. 219–224, Fort Lauderdale, Fla., February 1993] describe a four-layer silicon microfabricated hexagonal sheath flow channel. The channel is formed between two of the silicon wafers. Integrated optical waveguides intersecting the channel are used to couple laser light into the channel and out of the channel in the forward direction. At this intersection, the top and bottom walls of the channel are silicon nitride/silicon dioxide windows for 90° light collection. Each window is fabricated by growing an oxide layer on a silicon wafer, bonding the oxide layer to a second silicon wafer, etching away the silicon on both sides of the oxide at the window region and depositing a nitride layer. Sobek et al. [Proceedings of the Solid-State Sensors and Actuators Workshop, Hilton Head, S.C., June 1994] describe a sheath flow channel fabricated between two fused silica wafers. To couple light into the channel and out in the forward direction, optical fibers are sandwiched between the wafers orthogonal to the flow axis. Fluorescence is collected through the upper transparent wafer.

SUMMARY OF THE INVENTION

The present invention provides a flow cytometer made of two components: a flow cytometer optical head and a disposable flow module. The flow module utilizes a V-groove flow channel micromachined in a silicon wafer. The optical head comprises a laser and small and large angle photodetectors adapted for use with the V-groove flow channel. The flow module of this invention exploits the fact that anisotropic etching of single crystalline silicon wafers provides access to reflective surfaces with precisely etched angles relative to the surface of the wafer (Petersen, Proc. IEEE 70(5):420–457, 1982). These facets are used for reflecting, as opposed to transmitting, the illuminating laser beam. Small angle scattered light is also reflected by the V-groove wall and is collected by the small angle photodetector. Large angle scattered light and fluorescent light can exit the channel without reflection and are collected by the large angle photodetector. In addition, the reflective wall of the V-groove behind the illuminated particle enhances the fluorescence collection efficiency. Any part of the excitation beam that is not within the V-groove channel is reflected from the silicon surface in a direction away from either the small or large angle detectors.

Because the flow channel reflects the laser beam, rather than transmitting it, fabrication of the flow module of this invention is extremely simple. The microchannel is fabricated from a single wafer of silicon which is patterned on a single side. A transparent cover plate is attached to the top of the wafer to complete the module. Complex processing steps such as aligning and bonding multiple wafers and fabricating windows within silicon wafers are not required. Because the illuminating light enters the channel from the top rather than the side, optical waveguides built into the flow module are also not required.

Another advantage of the reflecting silicon channel is that it allows the light source and both photodetectors to be positioned above the plane of the silicon surface. This invention thereby allows the flow cytometer optical head, with its optical illuminating and collecting elements, to be housed separately from the flow module and fluid handling system. Because of the simplicity of fabrication and the separation from the optical elements, the flow module of this invention can be disposable. A used module can be removed from the optical head and easily replaced with a new one. A kinematic mount between the optical head and the flow module can be used for reproducible positioning. Optical realignment of the optical head is not required after replacing the flow module because the relevant aspect of the flow module, the reflective angle of the V-groove, is determined by the crystal structure of silicon and is precisely reproducible.

The flow cytometer optical head of this invention comprises a laser, a small angle detector and a large angle detector positioned for use with a V-groove flow channel. The optical elements are preferably mounted in a rigid housing to maintain their optical alignment. The optical head can be integrated on a silicon chip. The integrated optical head utilizes a diode laser and silicon waveguide as the light source, and silicon photodiodes to detect scattered or fluorescent light. Signal processing electronics can be further included on the chip. The flow module of this invention can be replaceably coupled with the optical head of this invention to provide a low cost flow cytometer for laboratory, clinical or field use.

BRIEF DESCRIPTION OF THE DRAWINGS

FIG. 2, comprising

DETAILED DESCRIPTION OF THE INVENTION

Figure 1:
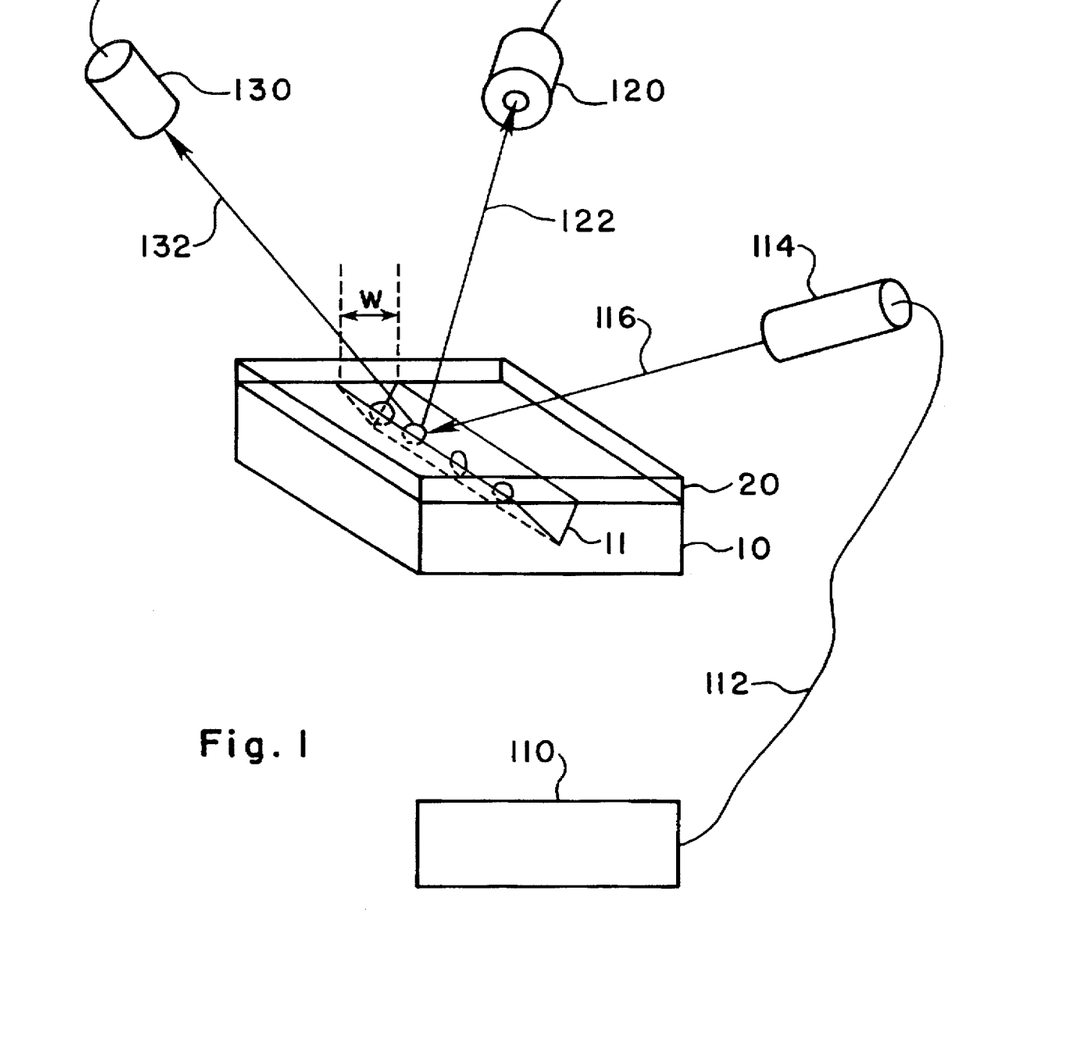
FIG. 1 shows the V-groove flow channel coupled with the flow cytometer optical head.

The V-groove channel of the flow module of this invention and the flow cytometer optical head of this invention are illustrated in FIG. 1. Elements of the flow module are labeled with numbers less than 100 and elements of the optical head are labeled with numbers greater than 100. Silicon wafer 10 has V-groove 11 therein. The term V-groove is used herein for a substantially "V" shaped groove in the surface of a silicon wafer. Depending of the fabrication process the point of the "V" can be flat (a trapezoidal groove), but only if the flat portion does not fall within the measurement zone defined by the interception of the illumination beam with the sample flow. In the preferred embodiment, wafer 10 has a <100> surface orientation and the walls of groove 11 are along <111> planes, providing an angle of 54.7° between the walls of the groove and the plane of the surface of the wafer. Transparent cover plate 20 is sealed to the surface of wafer 10. In the preferred embodiment the cover plate is made of pyrex and is anodically bonded to the silicon wafer.

Particle-containing sample fluid flows through the channel defined by V-groove 11 and the cover plate. The term particle is used herein for any solids within a fluid sample including, for example, cells and fluorescent labeled microspheres. The width of the top of the V-groove, w, is preferably small enough to force the particles into single file but large enough to pass the largest particles without clogging. For compliant particles such as cells, the width can be equal to the diameter of the largest particle, but is preferably one and one-half to two times the largest diameter. For example, for a mixture of 5 µm diameter red blood cells and 10 µm diameter white blood cells, a 15–20 µm channel width can be used. For rigid particles such as microspheres, the width at the top must be at least twice the diameter of the largest particle, and is preferably less than four times the diameter.

In an alternative embodiment, the sample fluid is hydrodynamically focused using a sheath flow. As is known in the art, for hydrodynamic focussing the sample fluid is injected into a stream of the sheath fluid and then the flow channel is constricted to reduce the diameter of the sample core. In this case the width of the channel at the measurement zone is many times larger than the largest particle, preferably >50 µm. Hydrodynamic focussing has the advantage of reducing channel clogging, but requires a more complex fluid inlet system. In either case laminar flow is preferred.

The flow cytometer optical head provides an illuminating laser beam 116. Beam 116 defines a measurement zone where it intercepts the sample fluid within the flow channel. Differences between the refractive indices of the various materials in the beam path, such as air, glass and sample fluid, alter the propagation direction of the beam. Bending of light rays at the interfaces is not illustrated in the drawing. Index matching materials can be used to provide direct coupling which minimizes reflection and refraction at interfaces. In the illustrated embodiment the light source includes diode laser 110, optical fiber 112 and focusing head 114. A typical beam diameter for a diode laser is 10–20 µm. Alternative lasers which can be used include argon ion, krypton ion, dye, helium-neon, helium-cadmium and YAG lasers. Commercially available diode lasers, typically having wavelengths in the 600–800 nm range, are suitable illumination sources for small and large angle scattering measurements. Since scattering efficiency increases as wavelength decreases, the shorter wavelengths are preferred. Although a few dyes can be excited with red light, fluorescence excitation typically requires light in the 300–600 nm range, for which frequency doubled diode lasers can be used.

Non-scattered light, i.e. light which has not been scattered by a particle, is specularly reflected by a wall of channel 11 and travels along path 122. Small angle (forward) scattered light deviates slightly from path 122 and impinges on small angle photodetector 120. In the illustrated embodiment, detector 120 is an annular detector having a beam stop in the center to block non-scattered light but collect light scattered at small angles. Some of the light scattered at large angles travels along path 132 to large angle photodetector 130. The photodetectors can be photodiodes or photomultipliers. Photodiodes are less expensive and more compact, while photomultipliers are more sensitive. Large angle detector 130 can be used to measure large angle scattering and/or fluorescence. It can contain a means, such as a spectrometer or a dichroic beamsplitter, for separating the excitation wavelength from the fluorescence wavelength. A plurality of large angle detectors can be used to measure different wavelengths. Lenses can be positioned in front of the detectors to collect and focus light.

The term small angle is used herein for angles greater than zero but less than 10° with respect to non-scattered direction 122. The small angle is more preferably between 0.5° and 5°. The term large angle is used herein for angles between 15° and 150° with respect to the non-scattered direction. The large angle is more preferably between 60° and 90°, and most preferably 90°, in order to minimize the amount of forward scattered light reaching the large angle detector. The small angle is chosen to be small enough to count the particles passing through the measurement zone and, preferably, to get a rough measurement of particle size from the scattering amplitude. The difference between the small and large angles is preferably large enough to give an indication of the particle size and structural complexity from the ratio of the scattering intensities.

There is a cone of rays at each angle relative to non-scattered ray 122. Annular detector 120 collects an entire cone of light. The placement of detector 130 at a point on the large angle cone is determined by which rays are not blocked by the channel walls and by space constraints. Detector 130 is positioned to avoid any part of beam 116 that does not land in the V-groove and is reflected by the surface of the silicon wafer. Detector 130 is optimally positioned such that back-reflection of fluorescent light from a wall of the V-groove into the detector enhances the collection efficiency.

Figure 2A:
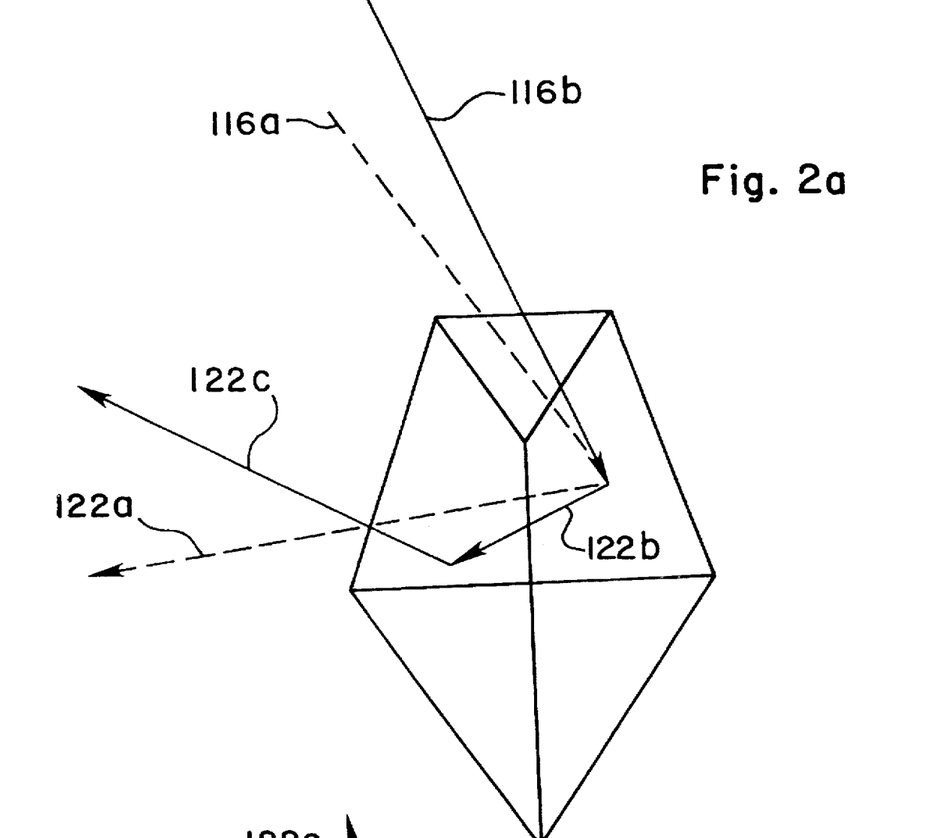
FIGS. 2a and 2b, shows optical pathways within the V-groove in (a) a perspective view and (b) an end view.
Figure 2B:
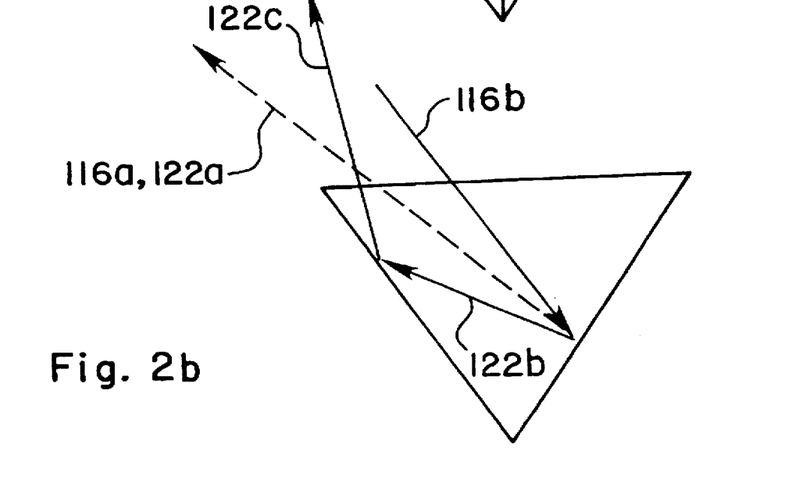

The optical path of the incident laser beam and its reflections within the V-groove is illustrated in the ray tracing diagram of FIG. 2. The dashed and solid lines represent beam paths for two different angles of incidence of the illuminating beam. The angle of incidence can be chosen to provide a single reflection from a wall of the V-groove, as shown by the path formed by dashed lines 116a and 122a. For different angles of incidence multiple reflections can be provided, as shown for the case of two reflections by the path formed by solid lines 116b, 122b, and 122c. To avoid multiple signals from a single particle, it is preferred that the beam path intercept a flowing particle only once or, alternatively, that the multiple intercepts occur simultaneously, i.e. in less than the detector response time. Note that if the beam intercepts a particle on path 122b, the large angle detector is positioned at a large angle with respect to line 122b but, because the forward scattered light also undergoes another reflection, the small angle detector is positioned with respect to line 122c. For a given optical separation, i.e., difference in angle between the collected small and large angle scattering, this reduces the physical separation between the respective detectors, i.e., the angle formed by the small angle detector, the measurement zone, and the large angle detector. Care must be taken to avoid reducing the physical separation between the detectors to the point where light scattered at a relatively small angle reaches the large angle detector and vice-versa. It is preferred that the physical separation between the two detectors be at least 30°.

In the preferred alignment, illuminating beam 116 and specularly reflected beam 122 are both in a plane normal to the V-groove and parallel to the channel axis. For light incident in this plane there is some shadowing of the bottom of the V-groove by the wall closer to the laser. However, since the particles are positioned in the upper portion of the V-groove, the shadowing does not block measurements. Beams 116 and 122 are preferably at about 90° (i.e. 80°–110°) to each other (about 45° with respect to the plane normal to the channel axis). Preferably detector 130 is positioned so that beam 132 is at about 90° with respect to beams 116 and 122.

In the description above, it is assumed that there is an index matching material between the laser and the cover plate so that reflection and refraction by the cover plate are minimized. If there is an air gap then, to avoid reflection by the cover plate, the incident beam should not be too shallow with respect to the cover plate surface. The angle of incidence on the cover plate must be selected to produce the desired angle at the V-groove. With an air gap, preferred angles of incidence on the cover plate are in the range of 10°–60° with respect to the plane normal to the channel axis and 30°–60° with respect to the cover plate surface.

Figure 3:
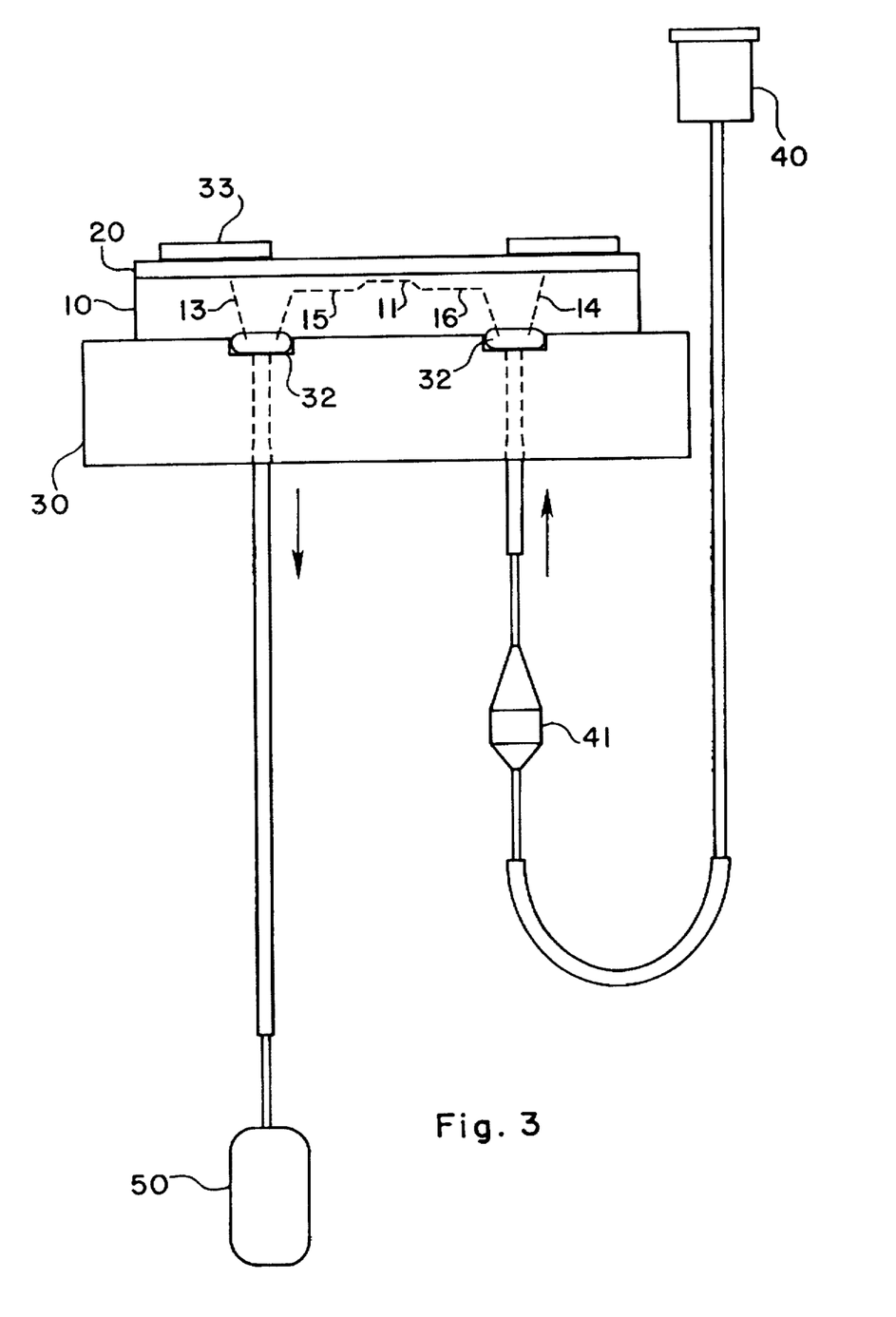
FIG. 3 is a side view of a flow module and the fluid handling system.
Figure 4:
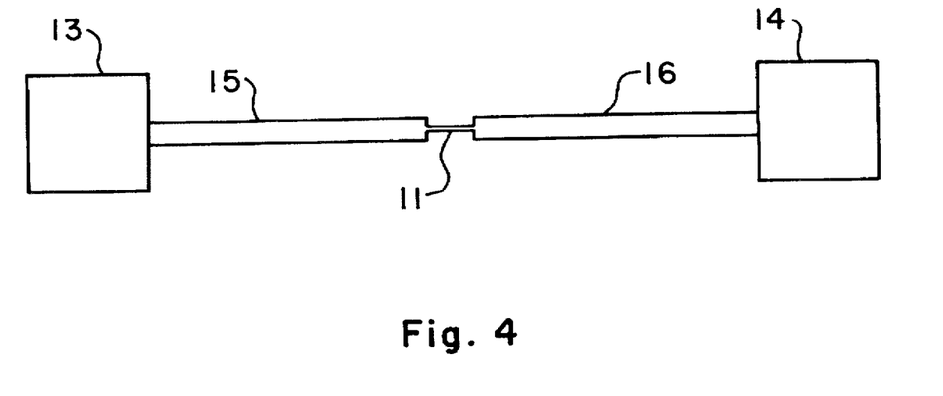
FIG. 4 is a top view of the etched features in the silicon wafer.

An embodiment of the flow module of this invention is shown in cross section in FIG. 3, and FIG. 4 shows a top view of the features etched in the silicon wafer. The flow module consists of silicon wafer 10 sealed to cover plate 20. Clamps 33 attach the flow module to holder 30. A fluid sample in supply container 40 flows through in line filter 41 and through the holder into fluid inlet port 14. The fluid flows through channels 16, 11 and 15 to fluid outlet port 13 and receiving container 50. The inlet and outlet ports are sealed with o-rings 32 to the holder. V-groove channel 11 is, in this embodiment, 25 μm wide at the top, about 20 μm deep, and 200–400 μm long. The length need only be longer than the illumination beam diameter (10–20 μm) and long enough to establish laminar flow. As the channel length increases more pressure is required to maintain the fluid flow. A means for applying pressure to the sample fluid can be used, such as a syringe or gravity feed. On either side of V-groove channel 11 are optional larger channels 15 and 16. In this embodiment they are trapezoidal channels 0.2 mm wide and about 50 μm deep.

In the illustrated embodiment the fluid inlet and outlet ports are etched through the wafer and the fluid enters from the bottom. As will be evident to those skilled in the art, many other configurations and fabrication techniques can be used. This embodiment does not utilize a sheath flow. When hydrodynamic focussing is desired, the channel width is greater and the fluid inlet port includes both a sheath fluid inlet and a sample fluid injection. The term fluid inlet (outlet) port is used herein for any element which couples sample fluid into (out of) the V-groove.

Silicon wafer 10 can be fabricated by techniques known in the semiconductor processing art. For example, to prepare a flow module a silicon wafer with a <100> surface was patterned with photolithography to make ports 13 and 14 in a first etching step and to make channels 11, 15 and 16 in a second step. An anisotropic etchant, EPW (ethylene diamine, pyrocatechol, water), was used, which creates the <111> planes of the V-groove walls. The V-groove stops forming once the junction of the <111> planes is reached. Anodic bonding was used to seal cover plate 20 to wafer 10. Other techniques for creating a V-groove can be used as known in the art. Crystals other than silicon can be used and will provide a different angle for the V-walls. For increased reflectivity, the walls of the V-groove can be coated with a reflective layer, such as a thin silver film. A protective overcoat can be used to prevent contact between the metal and the sample fluid.

For replacing flow modules, the silicon wafer preferably also includes a means for detachably coupling the flow module with the flow cytometer optical head with a reproducible alignment. Since it is the V-groove in the silicon wafer which is required to be aligned with the optical head, the alignment means is preferably patterned onto the silicon wafer using same mask as for the V-groove. As is known in the art, optical alignment markers can be etched into the silicon wafer. The wafer can be aligned by optical means and fixed into position after alignment. Specular reflection from the V-groove channel itself can be used to optimize alignment. An easier and more rapid technique is to etch features in the silicon surface which mechanically contact elements of the optical head structure. In the preferred embodiment the optical head includes a kinematic mount by which flow modules can be connected. The kinematic mount takes advantage of the flatness of silicon wafers and of the precisely etched angle of the V-groove to provide reproducible alignment.

Figure 5:
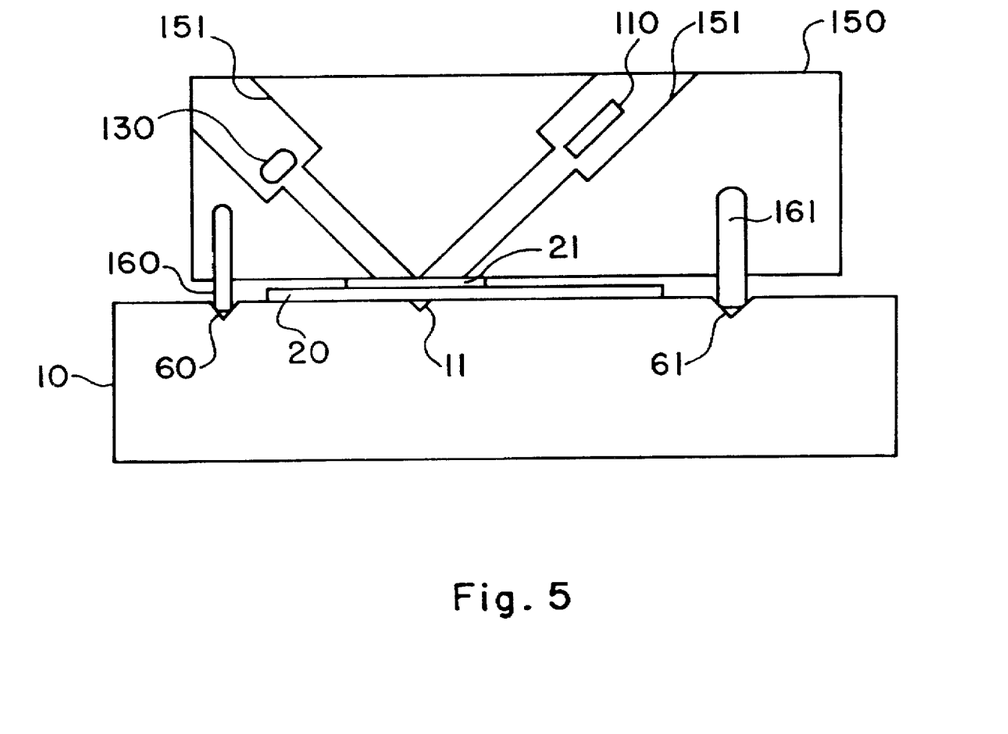
FIG. 5 is a side view of the flow module and the optical head connected by a kinematic mount.

An embodiment of the kinematic mount is illustrated in FIG. 5. In this side view drawing (not a true cross section in that not all these elements lie in a single plane) the reflection-mode optical head has a rigid housing 150 which holds laser 110 and detectors 120 (not shown) and 130 in cavities 151. Three pins protrude from the housing. The word pin is used herein for any protrusion, including a ball, rod, or pointed rod, which can mate with corresponding depressions. Two of these, 160 and 161, fit into precisely placed pyramidal pit 60 and groove 61 on wafer 10. The third pin (not shown) is shorter and simply touches the flat bare surface of the wafer at another point. Note that cover plate 20 is placed over flow channel 11 but places are maintained with bare silicon for the alignment features. In the preferred embodiment, transparent, compliant index-matching material 21 is interposed between the optical head and the flow module. Silicone gel has a well matched index of refraction with Pyrex and can be highly compliant, so that the distances are determined by the pin contacts and not the pressure of the gel on the cover plate. Use of an index-matching material removes variation in alignment caused by the variable thickness of pyrex cover plates. The kinematic mount makes rapid replacement of the flow module possible, while retaining precise alignment between the optical head and the V-groove flow channel. One embodiment of the kinematic mount is illustrated herein. As is known in the art, there are many kinematic mount designed.

The kinematic mount is illustrated as an integral part of the optical head. It can alternatively be on a separate holder which is fixed in position relative to the optical head.

Housing 150 can be a molded or machined metal or plastic block with a cavity to mount each of the optical elements. Index-matching gel can fill the balance of the cavity. Another way to house the optical head is to align each of the optical elements and position the pins of the kinematic mount and then pour around the elements a material which is rigid when hardened, such as a silicon elastomeric rubber. Although the rubber is not as rigid as metal, because the distances are so small and the mechanical loads so light, it is sufficiently rigid to maintain the optical alignment.

The optical head of this invention can be integrated on a silicon chip. The individual optical elements including a diode laser, wave guides, lenses, and photodiodes can be fabricated on silicon wafers, as is known in the art. They can be integrated together to make the integrated optical head of this invention.

EXAMPLE

Figure 6:
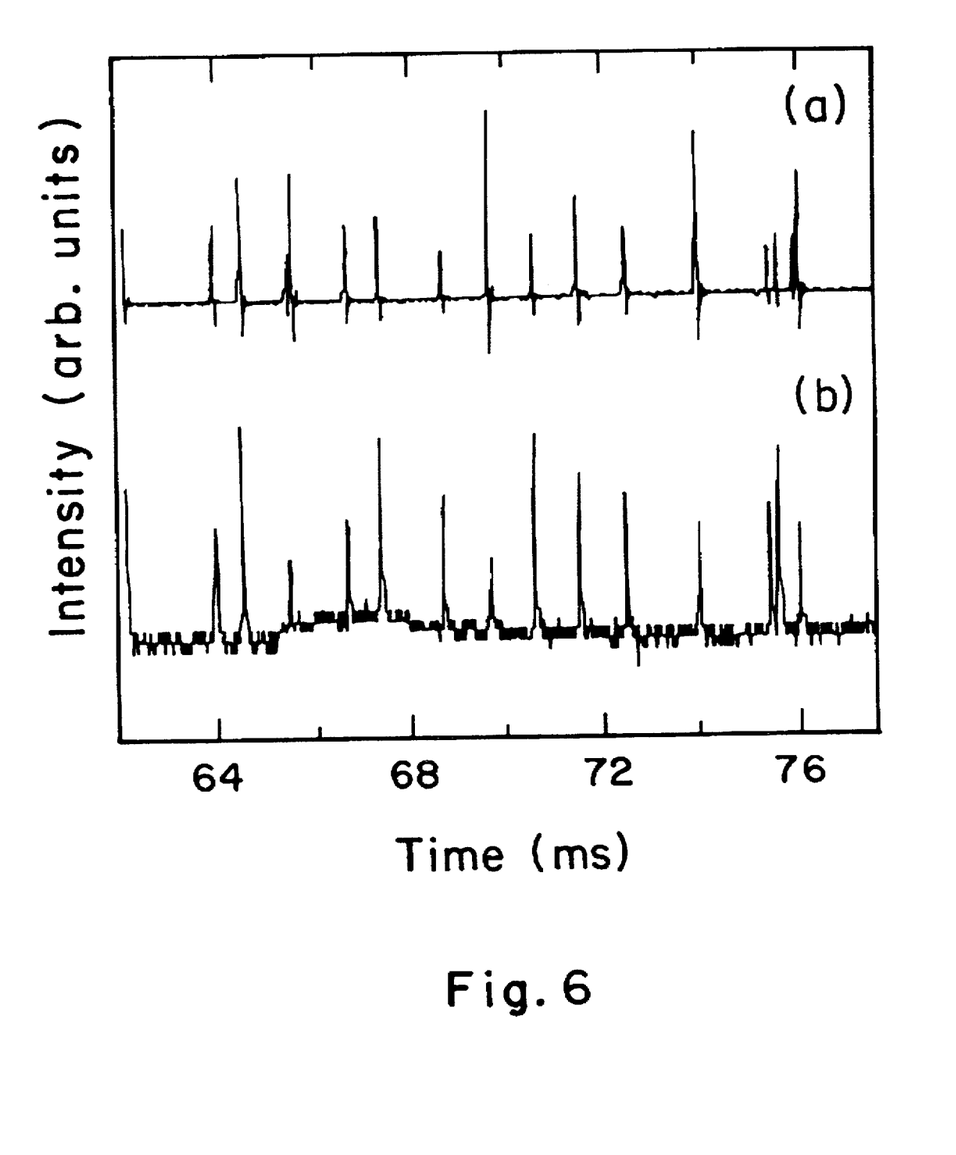
FIG. 6 is the measured (a) large and (b) small angle scattering by diluted whole blood.

Small and large angle scattering measured by a flow cytometer of this invention is shown in FIG. 6. The laser source was a 4 mW diode laser with wavelength 640 nm. The laser was coupled to an optical fiber, which was coupled to a focusing head assembly. No index-matching material was used. The power at the channel was about 1.2 mW with a 10–15 µm spot size. The laser beam was incident on the pyrex cover plate at an angle of 22° with respect to the plane normal to the channel axis and an angle of 45° with respect to the surface of the wafer. For this angle of incidence, the beam is reflected two times within the channel.

The two detectors were silicon PIN photodiodes with active areas of 31 mm$^2$. A 3 mm diameter disk of black tape was attached to the center of the small angle detector, which was positioned so that the non-scattered light fell on the black disk. The small angle detector collected light scattered at 5° to 10° with respect to the non-scattered light. The wide angle detector was positioned at an angle of about 60° with respect to the small angle detector. The width of the V-groove was 25 µm at the top. A 20 µm in line filer was used to screen particles bigger than the channel dimensions. The sample was whole blood diluted 1:20 so that only one red cell was in the measurement zone at a time. Large (FIG. 6a) and small (FIG. 6b) angle scattering was measured. The data do not show a large number of double or closely spaced peaks, indicating that the beam intercepts the particles in the channel only once. Peak counting indicates about 1000 counts/s. Analysis of the peaks indicates a consistent signal duration of about 100 µs, suggesting a flow rate of about 10 cm/s (using a laser spot size of 10 µm).

We claim:

1. A disposable flow module for use with a flow cytometer optical head, comprising:
   a silicon wafer having a surface, said wafer having formed therein:
   (1) a V-groove flow channel having a top with width w in the plane of said surface (thereof) and having first and second walls formed in said wafer;
   (2) a fluid inlet port coupled to a first end of said V-groove;
   (3) a fluid outlet port coupled to the second end of said V-groove; and
   (4) a module alignment means for detachably coupling said flow module with said optical head with reproducible optical alignment of said V-groove with said optical head; and
   a transparent cover plate sealed to said surface of said wafer and covering said V-groove, but not covering said alignment means.

2. The flow module of claim 1 adapted for use with a particle-containing fluid., said fluid having particles with largest diameter d, wherein said particles are compliant and wherein said width w is one and one half to two times said diameter d.

3. The flow module of claim 2 wherein said fluid is blood and wherein said width w is between 15 and 20 µm.

4. The flow module of claim 1 adapted for use with a particle-containing fluid, said fluid having particles with largest diameter d, wherein said particles are rigid and wherein said width w is two to four times said diameter d.

5. The flow module of claim 1 adapted for use with a sheath flow wherein said fluid inlet port comprises an inlet for a sheath flow and an inlet for injecting a particle-containing fluid core within said sheath flow, said fluid having particles with largest diameter d.

6. The flow module of claim 5 wherein said width w is at least three times said diameter d.

7. The flow module of claim 6 wherein said fluid is blood and wherein said width w is greater than or equal to 50 µm.

8. The flow module of claim 1 wherein said module alignment means comprises a groove in said surface of said wafer.

9. The flow module of claim 8 wherein said module alignment means comprises a plurality of grooves in said surface.

10. The flow module of claim 8 wherein said module alignment means further comprises a pit in said surface.

11. The flow module of claim 10 wherein said groove and said pit are configured to couple with a kinematic mount on said optical head.

12. The flow module of claim 11 wherein said groove is a V-groove and wherein said pit is pyramidal.

13. The flow module of claim 1 wherein said module alignment means and said V-groove are simultaneously etched onto said surface of said wafer.

14. The flow module of claim 1 wherein said surface of said wafer is a <100> surface and wherein said walls of said V-groove are <111> surfaces.

15. The flow module of claim 1 wherein said walls of said V-groove are coated with a reflective coating.

16. The flow module of claim 15 wherein said reflective coating is a metal thin film.

17. The flow module of claim 1 wherein said transparent cover plate is a glass plate.

18. The flow module of claim 17 wherein said glass plate is a pyrex plate.

19. The flow module of claim 18 wherein said pyrex plate is anodically bonded to said surface of said wafer.

20. A flow cytometer for analyzing a particle-containing fluid comprising the flow module of claim 1 and further comprising an optical head, said optical head comprising:
   a light source oriented to a direct a light beam onto said first wall of the V-groove, the angle of incidence of said light beam on said wall such that, in the absence of scattering by a particle, the non-scattered light beam is reflected at least once by said walls of said V-groove and is reflected out of said V-groove;
   a small angle photodetector oriented to receive light deviating by a small angle from the propagation direction of said non-scattered light beam;
   a large angle photodetector oriented to receive light deviating by a large angle from the propagation direction of said non-scattered light beam; and a mating alignment means for detachably coupling with said module alignment means.

21. The flow cytometer of claim 20 wherein said mating alignment means comprises a plurality of protruding pins.

22. The flow cytometer of claim 21 wherein said module alignment means comprises a groove and a pit in said surface of said wafer.

23. A flow cytometer optical head for analyzing a particle-containing fluid, said optical head adapted for use with the flow module of claim 1, comprising:
 a light source oriented to direct a light beam onto a said first wall of the V-groove, the angle of incidence of said light beam on said wall such that, in the absence of scattering by a particle, the non-scattered light beam is reflected at least once by said walls of said V-groove and is reflected out of said V-groove;
 a small angle photodetector oriented to receive light deviating by a small angle from the propagation direction of said non-scattered light beam;
 a large angle photodetector oriented to receive light deviating by a large angle from the propagation direction of said non-scattered light beam; and
 a mating alignment means for detachably coupling with said module alignment means.

24. The optical head of claim 23 wherein the incident beam is in a plane approximately normal to said wall and containing the channel axis of said V-groove.

25. The optical head of claim 24 wherein said incident beam is oriented at about 45° with respect to the plane normal to said channel axis.

26. The optical head of claim 25 wherein said small angle is less than about 10° and said large angle is about 90°.

27. The optical head of claim 23 wherein said small angle is less than about 10° and said large angle is between about 15° and 150°.

28. The optical head of claim 27 wherein said small angle is between about 0.5° and 5°.

29. The optical head of claim 27 wherein said large angle is between about 60° and 90°.

30. The optical head of claim 27 wherein said large angle is about 90°.

31. The optical head of claim 23 wherein said light source is a diode laser.

32. The optical head of claim 23 wherein said small angle photodetector is an annular detector positioned to receive said non-scattered light beam in its center.

33. The optical head of claim 32 wherein said small angle photodetector is a photodiode.

34. The optical head of claim 23 wherein said large angle photodetector includes a means for separating the wavelengths of received light.

35. The optical head of claim 34 wherein the separating means comprises a dichroic beamsplitter.

36. The optical head of claim 34 wherein said large angle photodetector comprises a plurality of photodetectore for the separated wavelengths of received light.

37. The optical head of claim 23 wherein said large angle photodetector is positioned to receive fluorescence from particles in said channel both directly and on reflection from the second wall of said V-groove.

38. The optical head of claim 23 further comprising a rigid housing on which said laser, said small angle photodetector and said large angle photodetector are mounted.

39. The optical head of claim 23 wherein said mating alignment means comprises a plurality of protruding pins.

40. The optical head of claim 39 wherein said pins form a kinematic mount.

41. A method of using the flow module of claim 1 to analyze a particle-containing fluid sample, comprising the steps of:
 providing the flow module of claim 1;
 utilizing said module alignment means to align said flow module with a light source;
 flowing a sample through said fluid inlet port, said V-groove and said fluid outlet port;
 impinging a light beam on said sample in said V-groove; and
 detecting light scattered at a small angle by said sample.

42. The method of claim 41 further comprising the step of detecting light scattered at a large angle by said sample.

43. The method of claim 41 further comprising the step of detecting fluorescence from said sample.

44. A flow cytometer optical head adapted for use with a V-groove flow channel, said V-groove having reflective walls, said V-groove for carrying a flow of particle-containing fluid, said optical head comprising:
 a light source oriented to direct a light beam onto a first wall of the V-groove, the angle of incidence of said light beam on said wall such that, in the absence of scattering by a particle, the non-scattered light beam is reflected at least once by the walls of said V-groove and is reflected out of said V-groove;
 a small angle photodetector oriented to receive light deviating by a small angle from the propagation direction of said non-scattered light beam; and
 a large angle photodetector oriented to receive light deviating by a large angle from the propagation direction of said non-scattered light beam.

45. The optical head of claim 44 wherein the incident beam is in a plane normal to said wall and containing the channel axis of said V-groove.

46. The optical head of claim 45 wherein said incident beam is oriented at about 45° with respect to the plane normal to said channel axis.

47. The optical head of claim 46 wherein said small angle is less than 10° and said large angle is about 90°.

48. The optical head of claim 44 wherein said small angle is less than 10° and said large angle is between 15° and 150°.

49. The optical head of claim 48 wherein said small angle is between 0.5° and 5°.

50. The optical head of claim 18 wherein said large angle is between 60° and 90°.

51. The optical head of claim 48 wherein said large angle is about 90°.

52. The optical head of claim 41 wherein said light source is a diode laser.

53. The optical head of claim 44 wherein said small angle photodetector is an annular detector positioned to receive said non-scattered light beam in its center.

54. The optical head of claim 53 wherein said small angle photodetector is a photodiode.

55. The optical head of claim 44 wherein said large angle photodetector includes a means for separating the wavelengths of received light.

56. The optical head of claim 55 wherein the separating means comprises a dichroic beamsplitter.

57. The optical head of claim 55 wherein said large angle photodetector comprises a plurality of photodetectors for the separated wavelengths of received light.

58. The optical head of claim 44 wherein said large angle photodetector is positioned to receive fluorescence from particles in said channel both directly and on reflection from the second wall of said V-groove.

59. The optical head of claim 44 further comprising a rigid housing on which said laser, said small angle photodetector and said large angle photodetector are mounted.

60. The optical head of claim 59 wherein said housing further comprises an alignment means for detachably coupling, with a reproducible alignment, said optical head with said V-groove flow channel.

61. The optical head of claim 60 wherein said alignment means comprises a plurality of protruding pins.

62. The optical head of claim 61 wherein said pins form a kinematic mount.

* * * * *

UNITED STATES PATENT AND TRADEMARK OFFICE
CERTIFICATE OF CORRECTION

PATENT NO. : 5,726,751

DATED : March 10, 1998

INVENTOR(S) : Altendorf and Yager

It is certified that error appears in the above-identified patent and that said Letters Patent is hereby corrected as shown below:

Column 10, line 45, please delete "claim 18" and replace with --claim 48--.

Column 10, line 49, please delete "claim 41" and replace with --claim 44--.

Signed and Sealed this

Thirtieth Day of June, 1998

Attest:

BRUCE LEHMAN

*Attesting Officer*     *Commissioner of Patents and Trademarks*